(12) United States Patent
Asirvatham et al.

(10) Patent No.: US 11,027,115 B2
(45) Date of Patent: Jun. 8, 2021

(54) SYSTEMS AND METHODS FOR ELECTROPORATION

(71) Applicant: Mayo Foundation for Medical Education and Research, Rochester, MN (US)

(72) Inventors: Samuel J. Asirvatham, Rochester, MN (US); Paul A. Friedman, Rochester, MN (US)

(73) Assignee: Mayo Foundation for Medical Education and Research, Rochester, MN (US)

(*) Notice: Subject to any disclaimer, the term of this patent is extended or adjusted under 35 U.S.C. 154(b) by 0 days.

(21) Appl. No.: 16/805,017

(22) Filed: Feb. 28, 2020

(65) Prior Publication Data

US 2020/0197687 A1 Jun. 25, 2020

Related U.S. Application Data

(63) Continuation of application No. PCT/US2018/057076, filed on Oct. 23, 2018.

(60) Provisional application No. 62/575,657, filed on Oct. 23, 2017.

(51) Int. Cl.
*A61N 1/04* (2006.01)
*A61B 5/024* (2006.01)
*A61B 5/053* (2021.01)

(52) U.S. Cl.
CPC ............ *A61N 1/0416* (2013.01); *A61B 5/024* (2013.01); *A61B 5/053* (2013.01)

(58) Field of Classification Search
CPC ........ A61N 1/0416; A61B 5/024; A61B 5/053
See application file for complete search history.

(56) References Cited

U.S. PATENT DOCUMENTS

| | | |
|---|---|---|
| 2007/0083239 A1 | 4/2007 | Demarais et al. |
| 2008/0119907 A1 | 5/2008 | Stahmann |
| 2013/0289369 A1 | 10/2013 | Margolis |
| 2013/0289650 A1 | 10/2013 | Karlsson et al. |
| 2014/0081259 A1 | 3/2014 | Deem et al. |

FOREIGN PATENT DOCUMENTS

WO   WO 2016/161201   10/2016

OTHER PUBLICATIONS

International Search Report & Written Opinion in International Application No. PCT/US2018/057076 dated Jan. 11, 2019, 17 pages.
International Preliminary Report on Patentability directed to related International Patent Application No. PCT/US2018/057076, dated Apr. 28, 2020; 7 pages.

*Primary Examiner* — Joseph M Dietrich
(74) *Attorney, Agent, or Firm* — Sterne, Kesler, Goldstein & Fox P.L.L.C.

(57) ABSTRACT

This document describes methods and materials for improving treatment of hypertension. For example, this document describes methods and devices for electroporation of nerves in the renal area to treat hypertension.

20 Claims, 3 Drawing Sheets

SYSTEMS AND METHODS FOR ELECTROPORATION

CROSS-REFERENCE TO RELATED APPLICATIONS

This application is a Continuation under 35 U.S.C. § 111(a) of International Application No. PCT/US2018/057076, filed on Oct. 23, 2018, which claims the benefit of U.S. Provisional Application Ser. No. 62/575,657, filed on Oct. 23, 2017. The disclosures of the prior applications are considered part of the disclosure of this application and are incorporated in their entirety into this application.

BACKGROUND

1. Technical Field

This document relates to methods and materials for improving treatment of hypertension. For example, this document relates to methods and devices for electroporation of nerves in the renal area to treat hypertension.

2. Background Information

Hypertension, commonly known as high blood pressure, is a long-term condition in which the blood pressure is persistently elevated and can affect 16-37% of the population globally. Long-term high blood pressure can be a major risk factor for coronary artery disease, stroke, heart failure, peripheral vascular disease, vision, and chronic kidney disease, to name a few. Lifestyle changes and medications can lower blood pressure and decrease the risk of health complications. Lifestyle changes can include weight loss, decreased salt intake, physical exercise, and a healthy diet. If lifestyle changes are not sufficient, then blood pressure medications can be used.

Syncope, commonly known as fainting, is a loss of consciousness and muscle strength characterized by a fast onset, short duration, and spontaneous recovery and can account for about three percent of visits to emergency departments, affect about three to six of every thousand people each year. Fainting can be caused by a decrease in blood flow to the brain, usually from low blood pressure. Treatment can include returning blood to the brain by positioning the person on the ground, with legs slightly elevated or leaning forward and the head between the knees. For individuals who have problems with chronic fainting spells, therapy can focus on recognizing the triggers and learning techniques to keep from fainting. At the appearance of warning signs, such as lightheadedness, nausea, or cold and clammy skin, counter-pressure maneuvers that can include gripping fingers into a fist, tensing the arms, and crossing the legs or squeezing the thighs together can be used to ward off a fainting spell.

The autonomic nervous system controls most of the involuntary reflexive activities of the human body. The system is constantly working to regulate the glands and many of the muscles of the body through the release or uptake of the neurotransmitters acetylcholine and norepinephrine. Autonomic dysregulation involves malfunctioning of the autonomic nervous system, the portion of the nervous system that conveys impulses between the blood vessels, heart, and all the organs in the chest, abdomen, and pelvis and the brain. Accordingly, autonomic dysregulation can play a major role in the genesis of hypertension and syncope.

SUMMARY

This document describes methods and materials for improving treatment of hypertension. For example, this document describes methods and devices for electroporation of nerves in the renal area to treat hypertension.

In one aspect, this disclosure is directed to a system for providing electroporation. The system can include a first electrode and a second electrode configured to be placed in a renal area of a patient, a sensor, and a pulse generator coupled to the first electrode, the second electrode, and the sensor. In some cases, the pulse generator can include a memory that is capable of storing computer executable instructions, and a processor that is configured to facilitate execution of the executable instructions stored in memory. The instructions can cause the processor to generate, via the pulse generator, a stimulation electrical current to cause stimulation between the first electrode and the second electrode, detect, via the sensor, a physiological response to the stimulation electrical current, and when the physiological response is detected, generate an electroporation electrical current to cause electroporation between the first electrode and the second electrode. In some cases, the physiological response can be a change in at least one of heart rate, blood pressure, transcutaneous impedance, and neural traffic in a peripheral nerve. In some cases, the renal area can include at least one of a renal vein, a renal artery, and a renal pelvis. In some cases, the instructions can further cause the processor to change an electrode configuration when no physiological response is detected. In some cases, changing the electrode configuration can include changing at least one of a location of the first electrode or the second electrode, changing a polarity of the first electrode or the second electrode, and changing a parameter for the stimulation electrical current. In some cases, the instructions can further cause the processor to generate, via the pulse generator, a second stimulation electrical current, and detect, via the sensor, a second physiological response to the second stimulation electrical current. In some cases, the system can include a third electrode configured to be located outside of the renal area. In some cases, the instructions can cause the processor to change both the first electrode and the second electrode to an anode or a cathode, change the third electrode to the other of the anode or the cathode, generate, via the pulse generator, a third stimulation electrical current, and detect, via the sensor, a third physiological response to the third stimulation electrical current. In some cases, the instructions can cause the processor to generate a second electroporation electrical current when the third physiological response is detected.

In another aspect, this disclosure is directed to a method of providing electroporation. The method can include placing a first electrode and a second electrode in a renal area of a patient, and generating an electroporation electrical current to cause electroporation between the first electrode and the second electrode. In some cases, the renal area can include at least one of a renal vein, a renal artery, and a renal pelvis. In some cases, the method can include generating a stimulation electrical current to cause stimulation between the first electrode and the second electrode. In some cases, the method can include detecting a physiological response to the stimulation electrical current. In some cases, the physiological response can be a change in at least one of heart rate, blood pressure, transcutaneous impedance, and neural traffic in a peripheral nerve. In some cases, the physiologic response can be assessed by an output of a supervised or unsupervised artificially intelligent network that incorporates multiple physiologic inputs. In some cases, the artificially intelligent network can be at least one of a feature extraction model, a hidden Markov model, a support vector machine, a convolutional neural network or a recurrent neural network. In some cases, the method can include changing an electrode configuration when the physiological response is detected. In some cases, changing the electrode configuration can include changing at least one of a location of the first electrode or the second electrode, changing a polarity of the first electrode of the second electrode, and changing a parameter for the stimulation. In some cases, the method can include generating a second stimulation electrical current to cause stimulation between the first electrode and the second electrode, and detecting a second physiological response to the second stimulation electrical current. In some cases, the method can include placing a third electrode outside the renal area. In some cases, the method can include changing both the first electrode and the second electrode to an anode or a cathode, changing the third electrode to the other of the anode or the cathode, generating a third stimulation electrical current, and detecting a third physiological response to the third stimulation electrical current. In some cases, the method can include generating a second electroporation electrical current when the third physiological response is detected.

In another aspect, this disclosure is directed to a system for providing electroporation. The system can include a memory that is capable of storing computer executable instructions, and a processor that is configured to facilitate execution of the executable instructions stored in memory. The instructions can cause the processor to generate an electroporation electrical current to cause electroporation between a first electrode and a second electrode configured to be located in a renal area of a patient. In some cases, the renal area can include at least one of a renal vein, a renal artery, and a renal pelvis. In some cases, the instructions can cause the processor to generate a stimulation electrical current to cause stimulation between the first electrode and the second electrode. In some cases, the instructions can cause the processor to detect a physiological response to the stimulation electrical current. In some cases, the physiological response can be a change in at least one of heart rate, blood pressure, transcutaneous impedance, and neural traffic in a peripheral nerve. In some cases, the instructions can cause the processor to change an electrode configuration when the physiological response is detected. In some cases, the method can include changing the electrode configuration comprising changing at least one of a location of the first electrode or the second electrode, changing a polarity of the first electrode or the second electrode, and changing a parameter for the stimulation. In some cases, the instructions can cause the processor to generate a second stimulation electrical current to cause stimulation between the first electrode and the second electrode, and detect a second physiological response to the second stimulation electrical current. In some cases, the instructions can cause the processor to change both the first electrode and the second electrode to an anode or a cathode, change a third electrode configured to be located outside the renal area to the other of the anode or the cathode, generate a third stimulation electrical current, and detect a third physiological response to the third stimulation electrical current. In some cases, the instructions can cause the processor to generate a second electroporation electrical current when the third physiological response is detected.

Particular embodiments of the subject matter described in this document can be implemented to realize one or more of the following advantages. The bipolar electroporation can provide sufficient energy to be effective without coming into contact with the structures to be electroporated. The architecture of tissues surrounding the energy delivery electrodes is not altered, minimizing complications. Further, the blood vessels are not burned, which can have detrimental side effects, such as damage to the vessel and/or coagulum. In addition, small amounts of DC energy can also minimize the risk of coagulum formation. By minimizing the risk of coagulum formation, electrodes can be placed in the blood vessels long term, providing extended electroporation.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described herein. All publications, patent applications, patents, and other references mentioned herein are incorporated by reference in their entirety. In case of conflict, the present specification, including definitions, will control. In addition, the materials, methods and examples are illustrative only and not intended to be limiting. The details of one or more embodiments of the invention are set forth in the accompanying drawings and the description below. Other features, objects, and advantages of the invention will be apparent from the description, the drawings, and the claims.

DESCRIPTION OF DRAWINGS

Like reference numbers represent corresponding parts throughout.

DETAILED DESCRIPTION

This document describes methods and materials for improving treatment of hypertension. For example, this document describes methods and devices for electroporation of nerves in the renal area to treat hypertension.

Autonomic dysregulation involves malfunctioning of the autonomic nervous system, the portion of the nervous system that conveys impulses between the blood vessels, heart, and all the organs in the chest, abdomen, and pelvis and the brain. Accordingly, autonomic dysregulation can play a major role in the genesis of hypertension and syncope.

The bipolar electroporation can provide sufficient energy to be effective without coming into contact with the structures to be electroporated. Further, the blood vessels are not burned, which can have detrimental side effects, such as damage to the vessel and/or coagulum. In addition, small amounts of DC energy can also minimize the risk of coagulum formation. By minimizing the risk of coagulum formation, electrodes can be placed in the blood vessels long term, providing extended electroporation.

Figure 2:
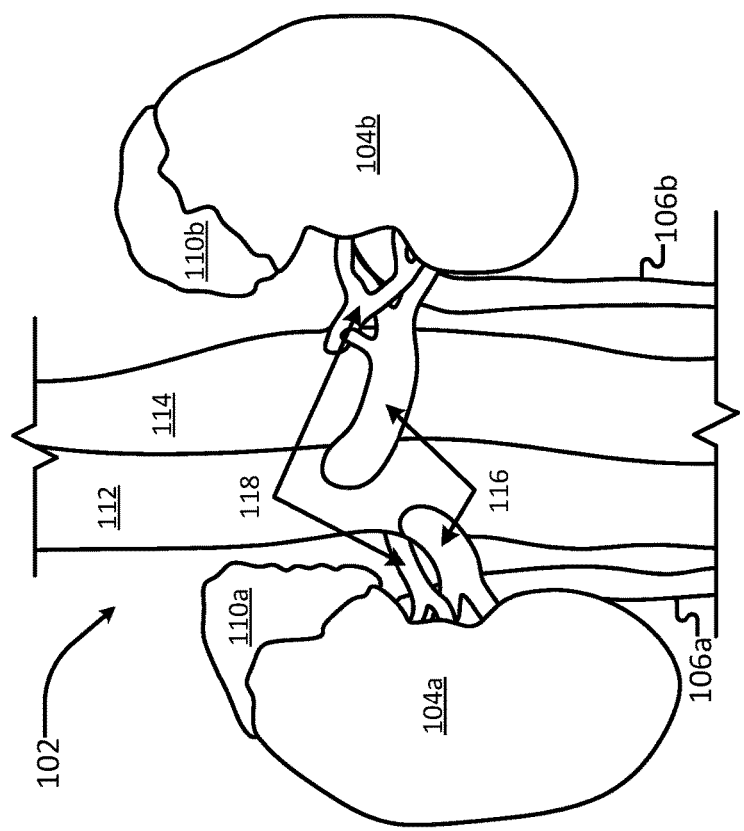
FIG. 2 is a schematic diagram of the renal area of FIG. 1, in accordance with some embodiments provided herein.
Figure 1:
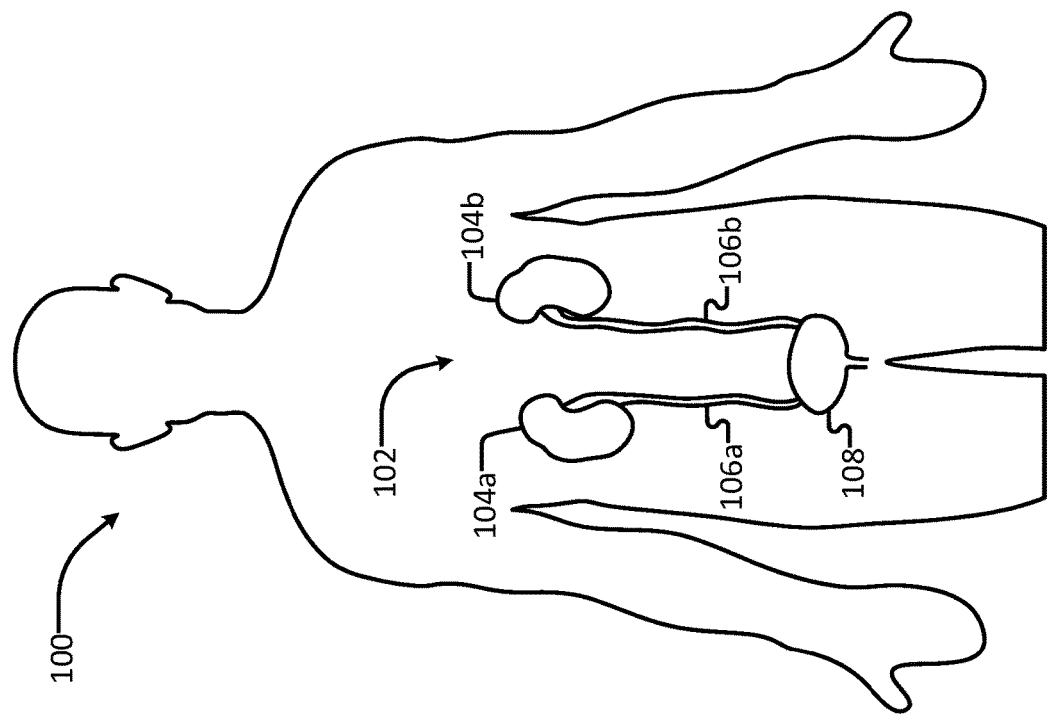
FIG. 1 is a schematic diagram of a person and a renal area, in accordance with some embodiments provided herein.

Referring to FIGS. 1 and 2, a person 100 has a renal area 102. The renal area 102 can include a right kidney 104a, and a left kidney 104b. Each kidney 104a and 104b can be attached to a ureter 106a and 106b, which can lead to a bladder 108.

Kidneys 104a and 104b can filter blood, release and/or retain water, remove waste, and control concentrations of the blood of person 100. The substances filtered out can be urine and can travel through the ureters 106a and 106b to the bladder 108. Ureters 106a and 106b can each include a renal pelvis (not shown). The renal pelvis can be a dilated portion of the ureters 106a and 106b that can attach to the kidneys 104a and 104b to create a basin for collecting waste and can aid in funneling the waste to the ureters 106a and 106b.

Kidneys 104a and 104b can each include an adrenal gland 110a and 110b, respectively. Adrenal glands 110a and 110b can produce and secrete hormones. Specifically, the adrenal glands 110a and 110b can produce aldosterone, which can aid in regulation of mineral balance and blood volume. Aldosterone can act on the kidneys 104a and 104b to cause changes in the reabsorption and/or excretion of sodium, potassium, and hydrogen ions. The amount of sodium present in the body can affect the extracellular volume, which in turn can influence blood pressure. Therefore, the effects of aldosterone in sodium retention can be important for the regulation of blood pressure. Accordingly, kidneys 104a and 104b can regulate blood pressure of person 100.

Kidneys 104a and 104b can receive blood from the renal arteries 118 via the descending aorta 114. The kidneys 104a and 104b can filter the blood received from the renal arteries 118 and can send the filtered blood to the inferior vena cava 112 via the renal veins 116 for distribution throughout the body, thus aiding in regulation of blood pressure.

Figure 3:
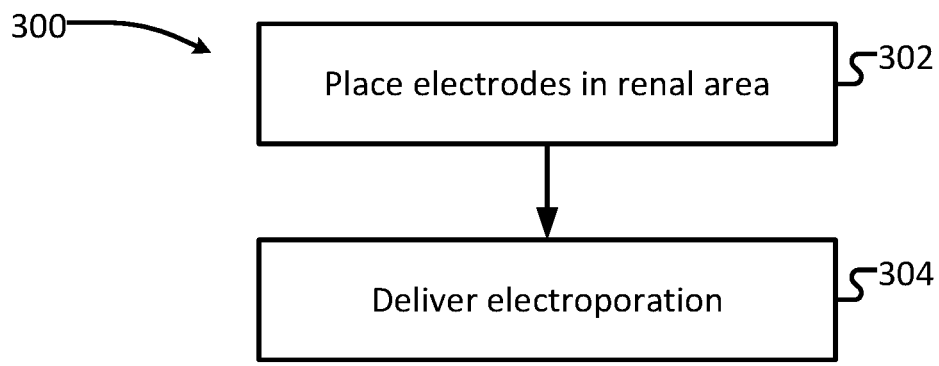
FIG. 3 is a method of electroporation of the renal area of FIG. 1, in accordance with some embodiments provided herein.

Referring to FIG. 3, a method 300 of electroporation of the renal area 102 of FIG. 1 can include placing an electrode in the renal area 102 at 302, and delivering electroporation at 304.

Placing an electrode in the renal area 102 at 302 can include placing one or more electrodes in the renal area 102. In some cases, an electrode(s) can be placed in a renal vein 116, a renal artery 118, a renal pelvis, a perimetric renal space, a parametric renal space, or a combination thereof. It is understood that in addition to the renal vein and renal artery, surrounding structures that may be anatomically situated in a favorable location to permit electric field distribution over the autonomic nerves of interest may be utilized, including the inferior vena cava, descending aorta, as well as the ureters themselves via retrograde or anterograde cannulation. In some cases, multiple electrodes can be placed in the renal area 102. In some cases, one or more electrodes can be on a skin of person 100. In some cases, electrodes can be placed inside the renal area 102 and on the skin of person 100. In some cases, retrograde ureterography can be used to place one or more electrodes. In some cases, laparoscopy can be used to place one or more electrodes. In some cases, a combination of implantation techniques can be used. In some cases, an electrode can be placed via a lead. In some cases, the lead can include multiple electrodes. In some cases, an electrode can be located on a balloon placed in the renal area 102. In some cases, a device with an electrode array can be placed in the renal area 102. In some cases, linear electrodes can be placed in the renal area 102. In some cases, an electrode cuff can be placed in the renal area 102. In some cases, the electrode can be an omnipolar (e.g., varying monopolar, bipolar, tripolar, etc.) electrode. In some cases, electrodes can be placed in other vascular structures. In some cases, electrodes can be placed in other nonvascular structures. In some cases, electrodes can be placed in a combination of vascular and nonvascular structures.

Delivering electroporation at 304 can include generating electrical pulses that can be delivered via the electrodes. In some cases, electroporation energy can be delivered with a high frequency. In some cases, electroporation energy can be delivered with a high voltage (e.g., 10 mV-100 V, or higher). In some cases, electroporation energy can be delivered as pulses with a pulse width in the nanoseconds. In some cases, electroporation can be delivered with a frequency and/or amplitude that causes reversible electroporation. In some cases, electroporation can be delivered with a frequency and/or amplitude that causes irreversible electroporation. In some cases, electroporation can be delivered by multiple electrodes in the renal area 102. In some cases, electroporation can be delivered by one or more electrodes in the renal area 102 and one or more electrodes outside the renal area 102. In some cases, electroporation can be delivered with different electrode configurations (e.g., varying location of electrodes, varying number of electrodes, varying polarity of electrodes, varying intensity of electroporation, etc.). In some cases, electroporation can be delivered between electrodes on the same device (e.g., balloon, lead, stent, catheter, etc.). In some cases, electroporation can be delivered between electrodes on different devices. In some cases, electroporation can reach a maximum intensity between electrode poles. In some cases electroporation energy is modulated so that energy delivery is synchronized to the QRS complex. This may avoid cardiac arrhythmia, to insure near-identical fluid volume during energy delivery, and to optimize similarity of electrode position with each energy pulse. In other embodiments energy pulsation is independently or additionally synchronized to respiratory activity.

Figure 4:
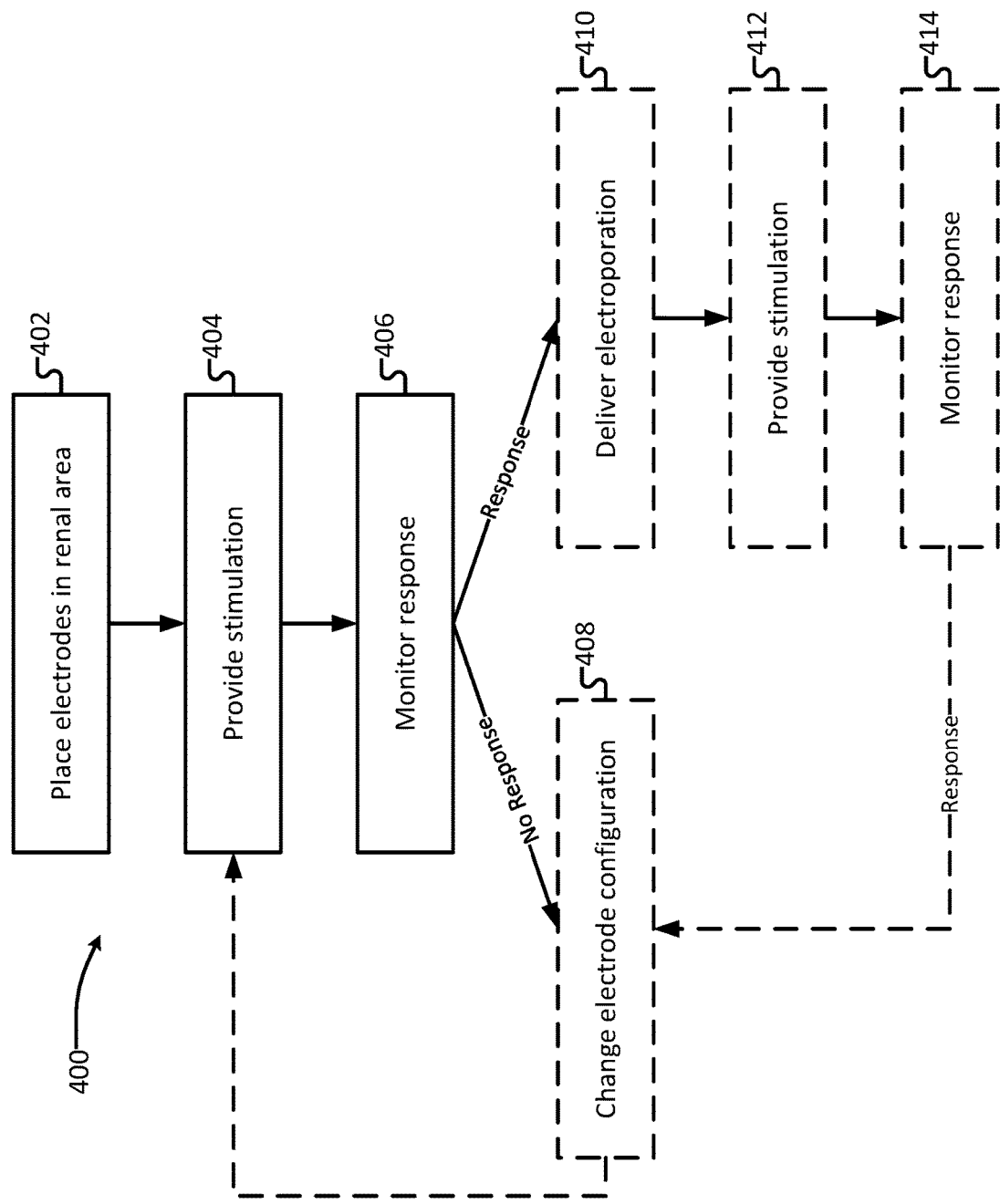
FIG. 4 is a method of targeting specific areas for electroporation of the renal area of FIG. 1, in accordance with some embodiments provided herein.

Referring to FIG. 4, a method 400 of targeting specific areas for delivering electroporation of the renal area of FIG. 1 can include placing an electrode in the renal area 102 at 402, providing stimulation at 404, and monitoring a response at 406.

Placing an electrode in the renal area 102 at 402 can be substantially similar to placing an electrode at 302 of method 300.

Providing stimulation at 404 can include generating an electrical pulse between electrodes. In some cases, the electrodes placed in the renal area 102 can provide stimulation and electroporation. In some cases, providing stimulation can include providing stimulation with a plurality of predefined electrode configurations. For example, providing stimulation can include going through multiple iterations of electrode configurations in a sequence while providing stimulation. In some cases, providing stimulation can include providing high frequency electrical pulses between electrodes.

Monitoring a response at 406 can include sensing one or more physiological responses to the stimulation provided at 404. In some cases, monitoring a response can include sensing one or more physiological responses to electroporation (e.g., electroporation at 304, 410, etc.). In some cases, monitoring a response can include placing sensory probes in or around a vessel (e.g., carotid vessels, brachial vessels). In some cases, monitoring a response can include using Doppler. In some cases, monitoring a response can include monitoring vascular changes. In some cases, monitoring a response can include monitoring neural effects. In some cases, monitoring a response can include placing an external sensing device on patient 100. In some cases, monitoring a response can include monitoring for a change (e.g., increase, decrease, overall change, crossing a threshold, amount of change crossing a threshold, etc.) in a physiological parameter. In some cases, the physiological parameter can include one or more of heart rate, blood pressure, transcutaneous impedance, neural traffic in peripheral nerves, etc. In some cases, monitoring a response can include monitoring a plurality of responses based on a plurality of electrode configuration and determining which configuration will lead to effective treatment upon electroporation based on the corresponding response. In some cases the response can be the output of a supervised or unsupervised artificially intelligent network that incorporates multiple physiologic inputs to determine response of therapy. Such networks may include hidden Markov models, support vector machines, or convolutional or recurrent neural networks.

If no response is detected at 406, method 400 can include changing an electrode configuration at 408. Changing an electrode configuration at 408 can include changing an intensity (e.g., pulse width, frequency, voltage, etc.) of electroporation or stimulation to be generated. In some cases, changing an electrode configuration can include moving the device holding the electrode(s) such that a location of the electrodes is changed. In some cases, changing an electrode configuration can include changing a polarity of one or more electrodes. In some cases, changing an electrode configuration can include changing a combination of electrodes selected to deliver electroporation and/or stimulation. In some cases, electrode configurations, intensity, or other stimulation parameters can be modified and if no response is detected after a plurality of configurations, the electrodes can be physically moved to change the location of the electrodes.

If a response is detected at 406, method 400 can include delivering electroporation at 410, providing stimulation at 412, and monitoring a response at 414.

Delivering electroporation at 410 can be substantially similar to delivering electroporation at 304 of method 300.

Providing stimulation at 412 may be substantially similar to providing stimulation at 404.

Monitoring a response at 414 may be substantially the same as monitoring a response at 406. If a response is detected at 414, method 400 can change the electrode configuration at 408. In some cases, if no response is detected at 414, method 400 can be considered complete. In some cases, if no response is detected at 414, an electrode configuration can be changed at 408 and method 400 can be repeated until no response is detected at 414 for a plurality of electrode configurations.

Figure 5:
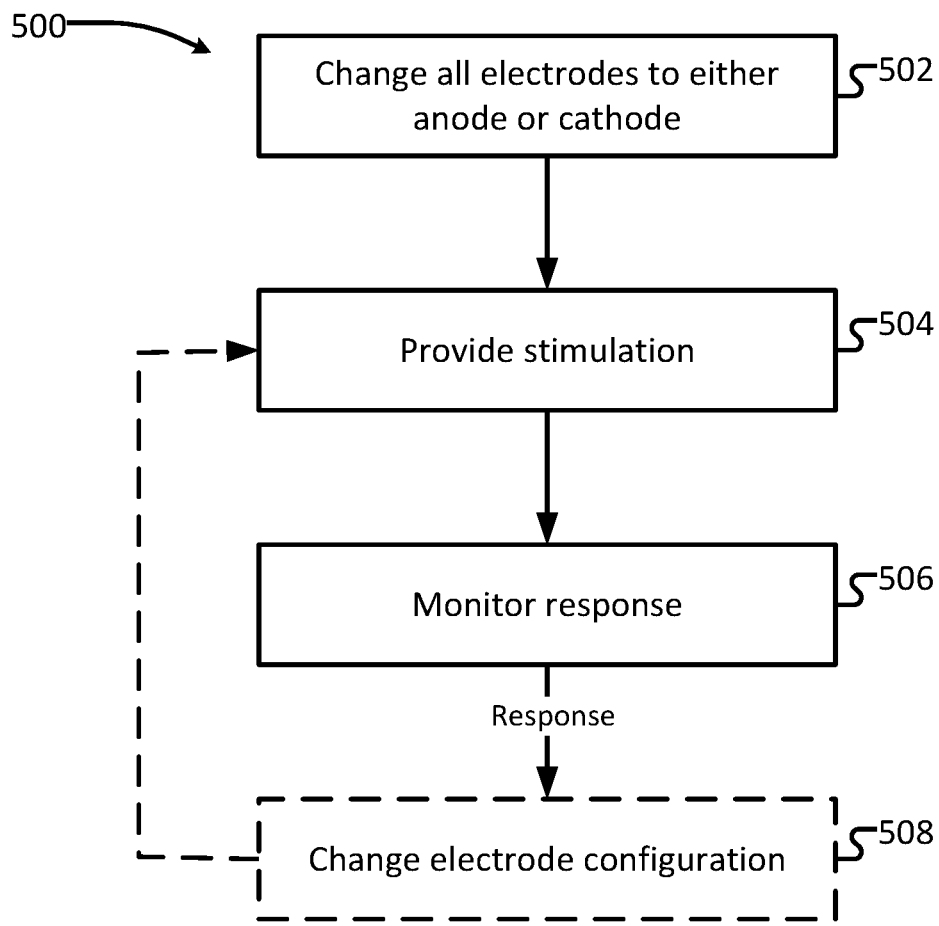
FIG. 5 is a method of confirming electroporation is effective, in accordance with some embodiments provided herein.

Referring to FIG. 5, a method 500 of confirming electroporation is effective can include changing all electrodes to either an anode or a cathode at 502, providing stimulation at 504, and monitoring a response at 506.

Changing all electrodes to either an anode or a cathode at 502 can include changing all internal active electrodes to either an anode or a cathode. In some cases, changing all electrodes to either an anode or a cathode can include changing a surface electrode to the other of a cathode or an anode. In some cases, the surface electrode can be external to the patient, such as on the skin of the patient. In some cases, the In some cases, changing all electrodes to either an anode or a cathode can include changing all of the active electrodes in the renal area to either an anode or a cathode and changing one or more electrodes outside the renal area to the other of an anode or a cathode.

Providing stimulation at 504 can be substantially similar providing stimulation at 404 of method 400.

Monitoring a response at 506 can be substantially similar to monitoring a response at 406 of method 400.

In some cases, method 500 can include changing an electrode configuration at 508 can be substantially similar to changing an electrode configuration at 408 of method 400. In some cases, changing an electrode configuration can include modifying a location of the electrodes. In some cases, modifying a location can include changing selected electrodes. In some cases, modifying a location can include moving a device on which the electrode is located.

In some cases, after multiple iterations of modifying the electrode configuration and still detecting a response when monitoring for a response, electroporation can be performed with all the internal electrodes set as either a cathode or an anode and a surface electrode set as the other of a cathode or an electrode.

In some cases, person 100 can be sedated during parts or all of the methods described herein. In some cases, the devices implanted for electroporation can be for single use, such that the devices are removed upon completion of one or more of methods 300, 400, and/or 500. In some cases, electroporation causes permanent, or substantially permanent effects.

In some cases, the devices implanted for electroporation can be implanted for long-term use. In some cases, long-term devices can manage blood pressure to prevent and/or reduce the effects and/or occurrences of high blood pressure and/or low blood pressure. In some cases, the implanted devices can include a subcutaneous generator. In some cases, the implanted devices can include sensors for measuring physiological signals (e.g., blood pressure, heart rate). In some cases, when the physiological signals crosses a threshold, the implanted devices can provide stimulation at selected locations. In some cases, devices can be permanently implanted in only the renal vein.

In some cases, balloon mounted electrodes can be used. In some cases, the balloon can provide irrigation. In some cases, the balloon can include embedded elements (e.g., electrodes, and injection ports). In some cases, the balloon can inject a calcium solution, autonomic chemical agents, enhancers of field strength, botulin toxins, saline, or other solutions. In some cases, the balloon can be shaped like a sea-urchin or porcupine, such that the balloon includes extension portions. In some cases, the extension portions can include an electrode and/or an irrigation port, which can increase the focus of electroporation.

In some cases, electroporation can be reversible. In some cases, electroporation can be irreversible. In some cases, reversible electroporation can be delivered to confirm location of stimulation and, accordingly, nerves, and then irreversible electroporation can be delivered.

In some cases, the devices and methods described above can be used near other sites of perivascular and/or autonomic neural tissue. For example, near the ganglia, such as in the cardiac spaces, the carotid vessels, the celiac ganglia, hepatic ganglia, and other sites. In some cases, the devices and methods can be located in the carotid region, internal and external to the jugular vein, in the pulmonary artery, in the aorta, in the epicardial space, in the hepatic vein or artery, in the portal vein, in the superior vena cava, or other veins and/or arteries. In some cases, modifying the location of the electrodes, and therefore the location of electroporation, can provide treatment of different disorders, such as obesity, diabetes, etc.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described herein should not be understood as requiring such separation in all embodiments, and it should be understood that the described program components and systems can generally be integrated together in a single product or packaged into multiple products.

Particular embodiments of the subject matter have been described. Other embodiments are within the scope of the following claims. For example, the actions recited in the claims can be performed in a different order and still achieve desirable results. As one example, the process depicted in the accompanying figures do not necessarily require the particular order shown, or sequential order, to achieve desirable results. In certain implementations, multitasking and parallel processing may be advantageous.

What is claimed is:

1. A system for providing electroporation, the system comprising:
   a first electrode and a second electrode configured to be placed in a renal area of a patient;
   a sensor; and
   a pulse generator coupled to the first electrode, the second electrode, and the sensor, the pulse generator comprising:
      a memory that is capable of storing computer executable instructions; and
      a processor that is configured to facilitate execution of the executable instructions stored in the memory, wherein the instructions cause the processor to:
         generate, via the pulse generator, a stimulation electrical current to cause stimulation between the first electrode and the second electrode for the renal area;
         detect, via the sensor, a change in blood pressure of the patient resulting from the stimulation electrical current; and
         in response to detecting the change in blood pressure of the patient, generate an electroporation electrical current to cause reversible or irreversible electroporation between the first electrode and the second electrode for the renal area.

2. The system of claim 1, wherein the renal area comprises at least one of a renal vein, a renal artery, and a renal pelvis.

3. The system of claim 1, wherein the instructions further cause the processor to change an electrode configuration when no change in blood pressure of the patient is detected.

4. The system of claim 3, wherein the changing the electrode configuration comprises at least one of changing a location of the first electrode or the second electrode, changing a polarity of the first electrode or the second electrode, and changing a parameter for the stimulation electrical current.

5. The system of claim 1, wherein the instructions further cause the processor to:
   generate, via the pulse generator, a second stimulation electrical current; and
   detect, via the sensor, a physiological response to the second stimulation electrical current.

6. The system of claim 1, further comprising a third electrode configured to be located outside of the renal area.

7. The system of claim 6, wherein the instructions further cause the processor to:
   change both the first electrode and the second electrode to an anode or a cathode;
   change the third electrode to the other of the anode or the cathode;
   generate, via the pulse generator, a second stimulation electrical current; and
   detect, via the sensor, a physiological response to the second stimulation electrical current.

8. The system of claim 7, wherein the instructions further cause the processor to generate a second electroporation electrical current in response to detecting the physiological response to the second stimulation electrical current.

9. The system of claim 1, wherein the first and second electrodes are configured to be placed near sites of autonomic nervous tissue in the renal area of the patient.

10. The system of claim 9, wherein the first and second electrodes are configured to permit electric field distribution over nerves adjacent the patient's inferior vena cava, descending aorta, or ureters.

11. The system of claim 1, wherein the electroporation electric current is configured to be delivered in pulses with a pulse width in nanoseconds.

12. The system of claim 5, wherein the physiological response is a change in at least one of heart rate, blood pressure, transcutaneous impedance, and neural traffic in a peripheral nerve.

13. A method of providing electroporation, the method comprising:
   placing a first electrode and a second electrode in a renal area of a patient;
   generating, via a pulse generator, a stimulation electrical current to cause stimulation between the first electrode and the second electrode for the renal area;
   detecting, via a sensor, a change in blood pressure of the patient resulting from the stimulation electrical current; and
   in response to detecting the change in blood pressure of the patient, generating an electroporation electrical current to cause reversible or irreversible electroporation between the first electrode and the second electrode for the renal area.

14. The method of claim 13, wherein the renal area comprises at least one of a renal vein, a renal artery, and a renal pelvis.

15. The method of claim 13, further comprising:
   changing an electrode configuration when no change in blood pressure of the patient is detected.

16. The method of claim 15 wherein the changing further comprises changing at least one of:
- a location of the first electrode or the second electrode,
- a polarity of the first electrode or the second electrode, and
- a parameter for the stimulation electrical current.

17. The method of claim 13, further comprising:
- generating a second stimulation electrical current to cause stimulation between the first electrode and the second electrode; and
- detecting a physiological response to the second stimulation electrical current.

18. The method of claim 13, further comprising placing a third electrode outside the renal area.

19. The method of claim 18, further comprising:
- changing both the first electrode and the second electrode to an anode or a cathode;
- changing the third electrode to the other of the anode or the cathode;
- generating, via the pulse generator, a second stimulation electrical current; and
- detecting a physiological response to the second stimulation electrical current.

20. The method of claim 19, further comprising generating a second electroporation electrical current in response to detecting the physiological response to the second stimulation electrical current.

* * * * *